United States Patent
Koch et al.

(10) Patent No.: US 8,529,530 B2
(45) Date of Patent: *Sep. 10, 2013

(54) DRAINAGE PUMP UNIT

(75) Inventors: Urs Koch, Greppen (CH); Ivo Ramella, Ebikon (CH); Fabian Joder, Baar (CH)

(73) Assignee: Medela Holding AG, Baar (CH)

( * ) Notice: Subject to any disclaimer, the term of this patent is extended or adjusted under 35 U.S.C. 154(b) by 753 days.

This patent is subject to a terminal disclaimer.

(21) Appl. No.: 12/271,652

(22) Filed: Nov. 14, 2008

(65) Prior Publication Data

US 2009/0157019 A1 Jun. 18, 2009

Related U.S. Application Data

(63) Continuation-in-part of application No. PCT/CH2007/000220, filed on May 3, 2007, and a continuation-in-part of application No. PCT/CH2008/000225, filed on May 16, 2008.

(30) Foreign Application Priority Data

May 9, 2006 (CH) .................................... 749/06
May 22, 2007 (CH) .................................. 00823/07

(51) Int. Cl.
*A61M 1/00* (2006.01)
(52) U.S. Cl.
USPC .......................................... 604/319; 604/540
(58) Field of Classification Search
USPC ........... 604/19, 313–324, 257–260, 540–543, 604/335; 4/144.3; 128/912; 417/4
See application file for complete search history.

(56) References Cited

U.S. PATENT DOCUMENTS

| 3,957,052 | A | 5/1976 | Topham |
| 4,883,476 | A | 11/1989 | Kurtz et al. |
| 5,466,229 | A | 11/1995 | Elson et al. |
| 5,507,734 | A | 4/1996 | Everett, Jr. et al. |
| 6,352,525 | B1 | 3/2002 | Wakabayashi |
| 6,358,218 | B1 | 3/2002 | Want et al. |

(Continued)

FOREIGN PATENT DOCUMENTS

| DE | 29911438 | 12/2000 |
| EP | 1184043 | 3/2002 |

(Continued)

OTHER PUBLICATIONS

International Search Report from European Application 09012685 mailed Dec. 11, 2009.

(Continued)

*Primary Examiner* — Jacqueline Stephens
*Assistant Examiner* — Benedict L Hanrahan
(74) *Attorney, Agent, or Firm* — McDonnell Boehnen Hulbert & Berghoff LLP

(57) ABSTRACT

The drainage pump unit according to the invention for aspirating body fluids by means of a suction pump comprises a drainage pump device with a pump housing (4) for receiving the suction pump, and a fluid collection container (5) that can be secured releasably on the pump housing (4). The drainage pump unit also comprises a pump-side attachment part (2) which has a connection element for connection to a patient-side drainage tube (10). The attachment part (2) is held releasably on the pump housing (4). This drainage pump unit allows the fluid collection container to be replaced without removing the drainage tube and, therefore, without disturbing the patient.

17 Claims, 15 Drawing Sheets

(56) References Cited

U.S. PATENT DOCUMENTS

| | | | |
|---|---|---|---|
| 6,394,996 B1 | 5/2002 | Lawrence et al. | |
| 6,755,807 B2* | 6/2004 | Risk et al. | 604/319 |
| 2001/0031943 A1* | 10/2001 | Urie | 604/43 |
| 2002/0058915 A1 | 5/2002 | Wakabayashi | |
| 2002/0161317 A1 | 10/2002 | Risk et al. | |
| 2003/0163101 A1 | 8/2003 | Say | |
| 2004/0024360 A1 | 2/2004 | Greter et al. | |
| 2004/0208756 A1* | 10/2004 | Adahan | 417/360 |
| 2005/0171495 A1 | 8/2005 | Austin et al. | |
| 2006/0036221 A1 | 2/2006 | Watson, Jr. | |

FOREIGN PATENT DOCUMENTS

| | | |
|---|---|---|
| EP | 1219311 | 7/2002 |
| GB | 2307180 | 5/1997 |
| GB | 2378734 A | 2/2009 |
| JP | 2001-507971 | 6/2001 |
| WO | 96/05873 | 2/1996 |
| WO | 98/30270 | 7/1998 |
| WO | 03/016719 | 2/2003 |
| WO | 2005/061025 | 7/2005 |
| WO | 2007/128156 | 11/2007 |

OTHER PUBLICATIONS

International Preliminary Report on Patentability for PCT/CH2007/000220 mailed on Dec. 10, 2008.

English translation of the Int. Preliminary Report on Patentability for International App. No. PCT/CH2008/000225, issued Dec. 7, 2009.

English translation of the Int. Search Report and Written Opinion for International App. No. PCT/CH2008/000225, dated Dec. 3, 2009.

English translation of the Int. Search Report and Written Opinion for International App. No. PCT/CH2007/000220, dated Dec. 4, 2008.

* cited by examiner

DRAINAGE PUMP UNIT

This application is a continuation-in-part of International application No. PCT/CH2007/000220 filed May 3, 2007, which claims priority to Swiss application No. 749/06 filed on May 9, 2006. This application is also a continuation-in-part of International application No. PCT/CH2008/000225 filed on May 16, 2008, which claims priority to Swiss application No. 00823/07 filed on May 22, 2007. The entire contents of each of these applications are incorporated by reference herein.

TECHNICAL FIELD

The invention relates to a drainage pump unit.

PRIOR ART

Drainage pump systems are used to aspirate body liquids and fluids in the medical field, for example during or after surgical interventions, but also in wound drainage, thorax drainage or liposuction. These drainage pump systems usually have a suction pump, one or more fluid collection containers and a drainage tube connection between patient and fluid collection container. The fluid collection container can be secured releasable on the housing of the drainage pump or can be connected to the pump via a vacuum tube.

With an underpressure being generated in the fluid collection container by means of the suction pump or vacuum pump, the fluid or secretion from a cavity in the patient is aspirated through the drainage tube and into the collection container and is collected therein. Filters arranged on the pump-side outlet of the collection container protect the suction pump from contamination by the aspirated fluid. A fluid collection container of this kind with a rigid cover and with a flexible bag secured thereon is known, for example, from EP 0 861 668 and WO 01/24846.

EP 0 466 334 discloses a drainage line with a drainage catheter and an airtight sleeve surrounding the catheter. At both of its ends, the catheter is connected to an attachment part. A connector for a gas analyzer is provided on the patient-side attachment part.

In addition to the drainage line, it is also known to run a service line from the pump to the patient. For example, U.S. Pat. No. 5,738,656 uses a double-lumen tube, one lumen forming the drainage line, and the second lumen being an air conduit which, at the patient-side end, opens into the drainage line. In this way, air or gas can be fed into the patient cavity to be aspirated, and the cavity can thus be flushed. This lumen can additionally be used as a measurement line for determining flow differences or pressure differences. In this way, the drainage procedure can be optimally monitored and also automatically controlled.

In WO 05/061025, a service line connected to the patient-side end of the drainage tube is used to flush the drainage line, in order to avoid or to eliminate occlusion of the line by aspirated clots or tissues.

U.S. Pat. No. 6,626,827 describes a drainage tube unit with two tubes, which drainage tube unit has a y-shaped attachment part at the pump-side end. At the patient-side end, the two tubes open into two independent attachment parts.

U.S. Pat. No. 5,029,580 discloses a drainage tube unit with a double-lumen tube, which contains a drainage line and an air delivery line. At the patient-side end, the tube has internal through-openings that connect the two lines to each other. At its ends, this tube is provided with a pump-side attachment part and a patient-side attachment part. Further connection possibilities are also provided in these attachment parts.

U.S. Pat. No. 5,134,996 discloses a multi-lumen drainage tube which is surrounded by a sleeve and which, at its two ends, is provided with attachment parts.

Although these connectors, by virtue of their attachment parts, avoid incorrect manipulations, they nevertheless have a relatively complicated structure, particularly since they are composed of a plurality of individual parts. In addition, they can also only be used with a double-lumen catheter tube, in particular only with a tube that has a specially designed patient-side end. However, since these drainage tube units cannot be used more than once and are discarded as disposable parts after one use, they have to be as inexpensive as possible.

A disadvantage of the systems according to the prior art is, furthermore, that the drainage tubes always have to be removed from the fluid collection container when the latter is emptied. This causes unnecessary disturbance of the patient.

SUMMARY OF THE INVENTION

It is therefore an object of the invention to make available a drainage pump unit that reduces disturbance of the patient to a minimum.

This object is achieved by a drainage pump unit
for aspiration body fluids of a patient, said drainage pump comprising:
a suction pump;
a pump housing accommodating said suction pump;
a fluid collection container releasably secured on said pump housing and
a drainage tube for draining said aspirated fluid into said fluid collection container, said drainage tube having a first end and a second end, said first end being connectable to said patient and said second end being releasably arranged in said pump housing.

In another aspect of the invention the drainage pump unit for aspiration body fluids of a patient comprises
a suction pump;
a pump housing accommodating said suction pump;
a fluid collection container releasably secured on said pump housing and
a pump-side attachment part which has a connection element for connection to a patient-side drainage tube, wherein said attachment part is held releasably on said pump housing.

In another aspect of the invention the drainage pump unit for aspirating body fluids by means of a suction pump comprises a drainage pump device with a pump housing for receiving said suction pump, and a fluid collection container that can be secured releasably on said pump housing, wherein said drainage pump housing also comprises a recess for accommodating a pump-side attachment part, said pump-side attachment part having a connection element for connection to a patient-side drainage tube, wherein said pump-side attachment part is held releasably on said pump housing.

According to another aspect of the invention, a portable aspiration pump unit for the aspiration of bodily fluids and/or air has a pump assembly housing with a pump assembly and at least one fluid collection reservoir detachably connected to this pump assembly housing, wherein said pump assembly housing has a front wall, a rear wall, and a side wall arranged between said two walls, and wherein a connector for a patient's tube can be arranged in one of said walls.

In a preferred embodiment the attachment part is held releasably on the pump housing and it has a connector piece onto which an attachment opening of the fluid collection container can be fitted. Alternatively, the attachment part can have an attachment opening into which a connector piece of the fluid collection container can be inserted. The connection element and the connector piece or attachment opening are connected to each other via a drainage channel extending through the attachment part.

Since the drainage tube or the attachment part is not now held in the fluid collection container, but instead in or on the pump housing, and can be connected to the fluid collection container, the fluid collection container can be removed and emptied or replaced, without the drainage tube having to be removed. It can remain inserted in the pump housing. The patient is therefore not inconvenienced, since the drainage tube does not have to be touched or moved.

The connection between pump-side attachment part and fluid collection container is preferably made directly, i.e. without intermediate tubes or intermediate conduits.

The pump housing preferably has a recess in which the attachment part is held releasably and, in particular, into which it can be plugged. In this way, the attachment part is held securely and is also not moved upon release of the fluid collection container.

In a preferred embodiment, the recess is located in a wall of the pump housing directed towards the fluid collection container. The recess preferably extends as far as an edge of the wall and thus forms a corner piece. It is advantageous if the edge is an upper edge.

The attachment part is preferably held in a form-fit engagement in the recess of the pump housing.

The recess in the pump housing preferably has a substantially cuboid shape, and the attachment part has a substantially cuboid main body.

In a preferred embodiment, the connection element and the connector piece or attachment opening are arranged on two different sides of the attachment part, in particular on two sides lying at right angles to each other.

The pump-side attachment part is preferably designed in one piece.

In a preferred embodiment, the pump-side attachment part or pump-side end connector has a patient-side connection element for connection to a service tube, a pump-side connection element for connection to a service unit arranged in the pump housing, and a service channel that connects these two connection means and extends through the attachment part. The patient-side connection element for connection to the service tube and the connection element for connection to the patient-side drainage tube are preferably arranged on the same side of the attachment part. The connection between pump-side attachment part and pump housing is also preferably made without connection tubes or intermediate tubes.

In a preferred embodiment, the portable suction or aspiration pump unit for the aspiration of bodily fluids and/or air, has a pump assembly housing with a pump assembly and at least one secretion or fluid collection reservoir detachably connected to this pump assembly housing. The pump assembly housing has a front wall, a rear wall, and a side wall arranged between these two walls, while the front wall and the rear wall each have one wall edge projecting beyond this side wall, and the fluid collection reservoir or container is held between these wall edges. In this way, the fluid collection reservoir can be secured easily to the pump assembly housing, yet be held firmly and protected inside it.

The patient can carry the aspiration pump unit around with him or her in many different ways. He can hang it from his neck by a strap, fasten it to a belt, or wear it over the shoulder by a strap. If he is bedridden, he can place the unit on a table or simply hang it from the bed.

What is more, fluid collection reservoirs of different size can be used with the same housing. This allows one to lower the fabrication and operating expenses.

In one preferred embodiment, the fluid collection reservoir is held and can swivel in and out between the wall edges. Preferably, the reservoir is held and hinged in a lower region and can be locked to the pump assembly housing in an upper region.

Preferably, the reservoir can be removed entirely from the housing. Replacement of the reservoir is facilitated if the reservoir can be snapped into the housing.

The invented aspiration pump unit is used for medical purposes, especially for thoracic drainage and for wound drainage. However, other areas of application are possible, for example, for the aspiration of bodily fluids during surgery or for liposuction.

Especially in the case of thoracic and wound drainage it is beneficial for the device to remain in constant operation so that a permanent vacuum can be applied, which is actively maintained. Not only does this speed up the healing, but also it lowers the operating expenses, since the device is not used as long and therefore does not have to be rented for as long as the conventional device.

In a preferred embodiment, a fluid collection reservoir is used for aspiration pump units of said type, which prevents contamination of the suction line or of the suction pump with aspirated fluid.

This fluid collection reservoir has a secretion connector for connecting a drainage line located at the patient's side and a vacuum connector for connecting to a suction pump. The reservoir has an interior space which is divided by means of ribs, with the interior space being divided at least into a vacuum chamber and a secretion chamber, with said two chambers being connected to one another by means of at least one narrow passage, and with the vacuum connector being arranged in the vacuum chamber and the secretion connector being arranged in the secretion chamber.

The vacuum chamber and the secretion chamber are preferably not connected to one another directly, but rather an intermediate chamber is connected in between. An inclined rib is preferably also provided in the upper region of the secretion chamber, below the vacuum chamber, which inclined rib prevents the fluid from surging up.

As a result of the division of the vacuum chamber and secretion chamber, the vacuum connector is relatively well protected, even without non-return valves or membranes.

Other advantageous embodiments will become evident from the dependent patent claims.

BRIEF DESCRIPTION OF THE DRAWINGS

The subject matter of the invention is explained below on the basis of preferred illustrative embodiments depicted in the attached drawings, in which is shown:

FIG. 14, a perspective view through a drainage tube unit according to

FIG. 13 when sectioned in the longitudinal direction;

WAYS OF IMPLEMENTING THE INVENTION

Figure 1:
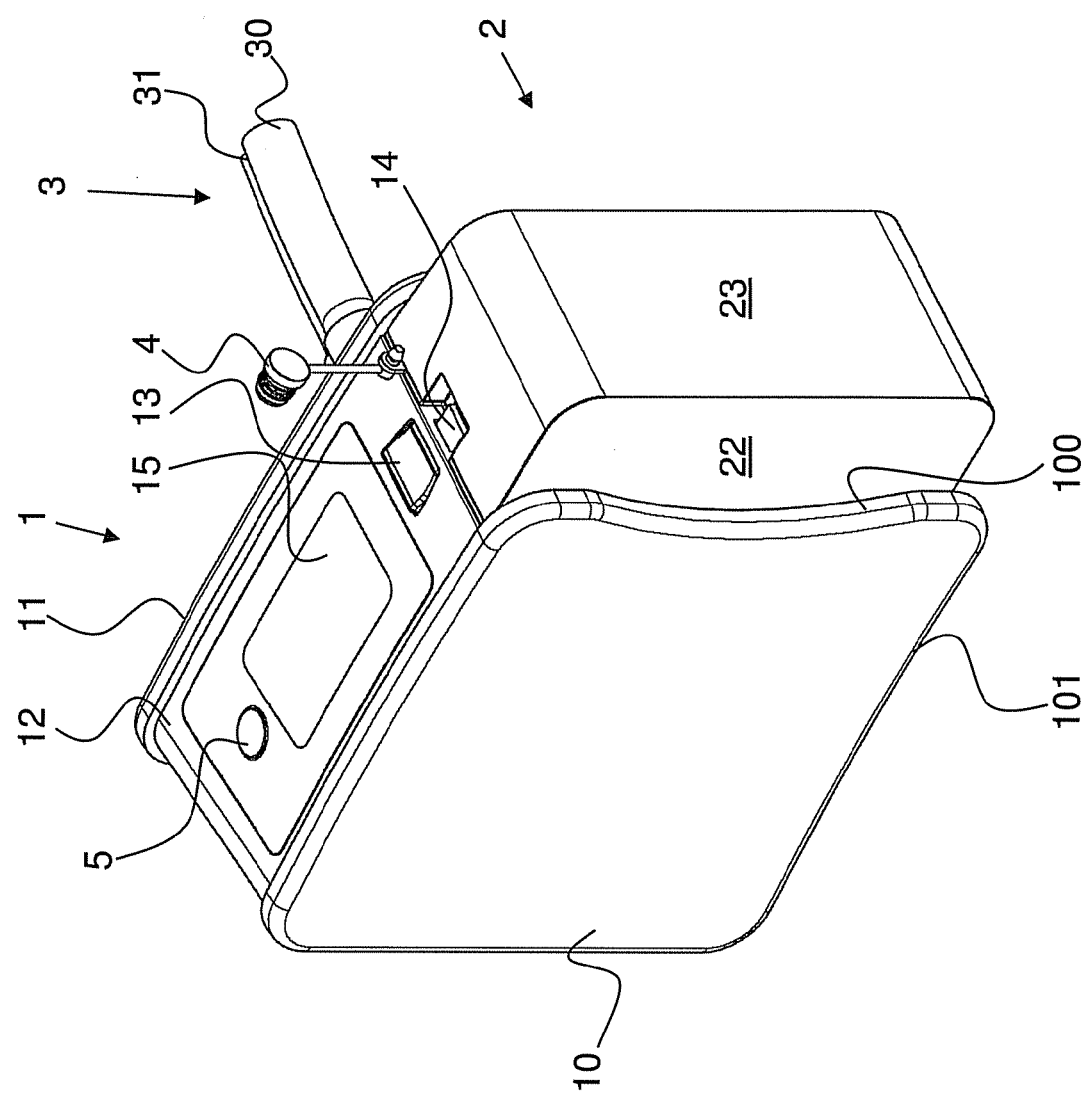
FIG. 1, a perspective view of an aspiration pump unit according to the invention in a first embodiment.
Figure 2:
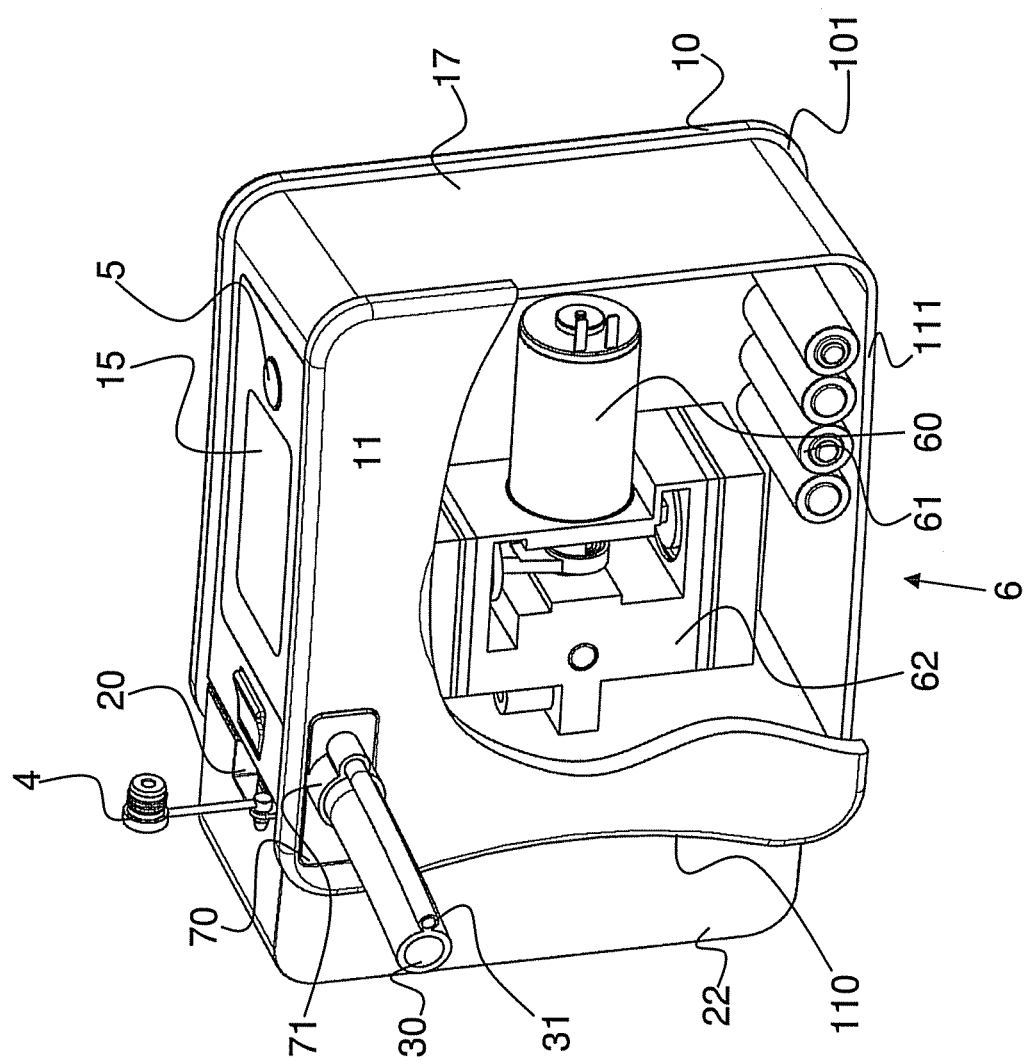
FIG. 2, the aspiration pump unit of FIG. 1, looking into the interior of the housing.

FIGS. 1 and 2 show a first sample embodiment of the invented suction or aspiration pump unit. It consists essentially of a pump assembly housing 1 with a pump assembly 6 arranged therein and visible in FIG. 2 and at least one fluid collection reservoir 2. Preferably, there is exactly one fluid collection reservoir 2 present. The pump assembly 6 serves to create the partial vacuum necessary for the aspiration. The fluid collection reservoir 2 can be connected to the pump assembly 6, so that the partial vacuum can be created in the reservoir 2. The collection reservoir 2 is connected via an aspiration tube or a secretion line 30 to a cavity or wound of the patient, from which it is needed to aspirate the bodily fluid, while the reservoir 2 collects the aspirated bodily fluid.

Preferably, not only the drainage tube or secretion line 30 goes to the patient, but so does a service tube or metering line 31, by which the pressure, for example, or the quantity of flow in the secretion line can be measured. For this, preferably, a double-lumen patient tube 3 is used, which contains both lines 30, 31. The tube 3 can be led out in a straight line from the housing 1, as depicted here. However, it can also be arranged with a bend, or one can use a bent adapter piece in which the tube 3 can be inserted.

Figure 7:
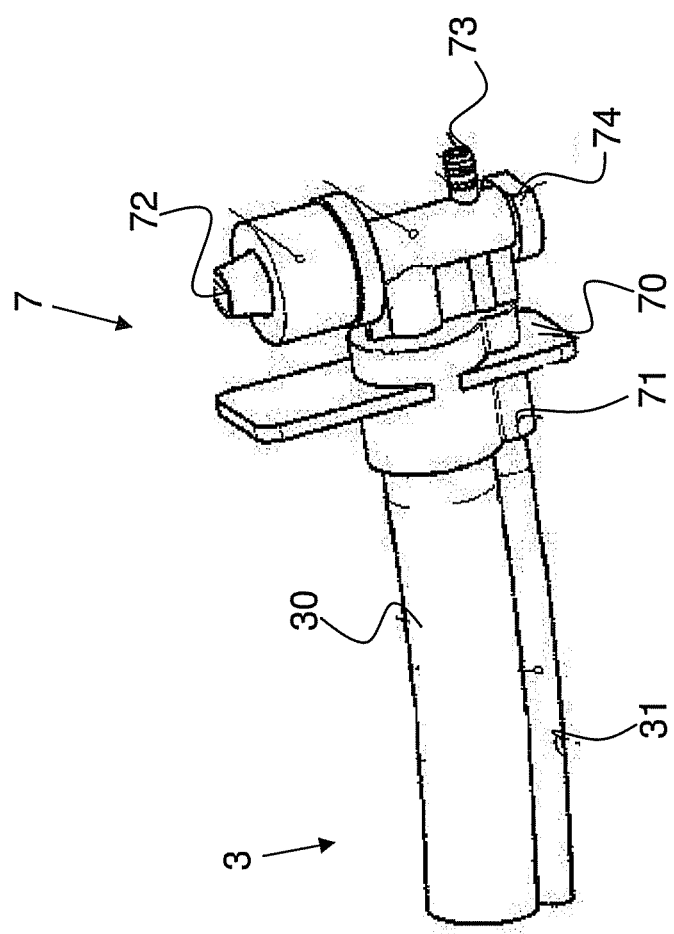
FIG. 7, a perspective representation of an adapter according to the invention, for a tube located at the patient's side.

Preferably, the tube 3 is placed onto a connector or an adapter or an attachment part 7. This adapter or attachment part is shown in detail in FIG. 7. It is preferably made of plastic by means of an injection molding technique. It has a double pipe connector piece 71, on or in which the double-lumen patient's tube 3 can be inserted. A flange 70 is molded on this pipe connector piece 71, which lies against the housing 1 and by means of which the adapter 7 can be secured in the housing 1, for example, by clamping. The part of the adapter 7 inside the housing has a bent coupling piece 72 for a secretion connector 19 at the housing and a connection piece 73 for the metering line 31 or lines. The end 74 opposite the coupling piece 72 is closed.

The pump assembly 6 basically consists of an electric motor 60, a storage element 61, here, batteries, and a vacuum pump 62. The motor 60 is preferably flanged onto the pump 62 and the vacuum pump 62 is preferably secured onto the housing 1. All familiar pumps of sufficiently small size and having enough power for the corresponding application are suitable. The flow rate is preferably around 5 l/min. Preferably, a dual-action membrane pump is used.

The assembly 6 is preferably arranged approximately in the middle or center of the housing 1. It is beneficial for the assembly 6 to be arranged such that the common center of gravity of the housing 1 and the assembly 6 prevents the housing 1 from tilting to the side when one is carrying it.

Figure 3:
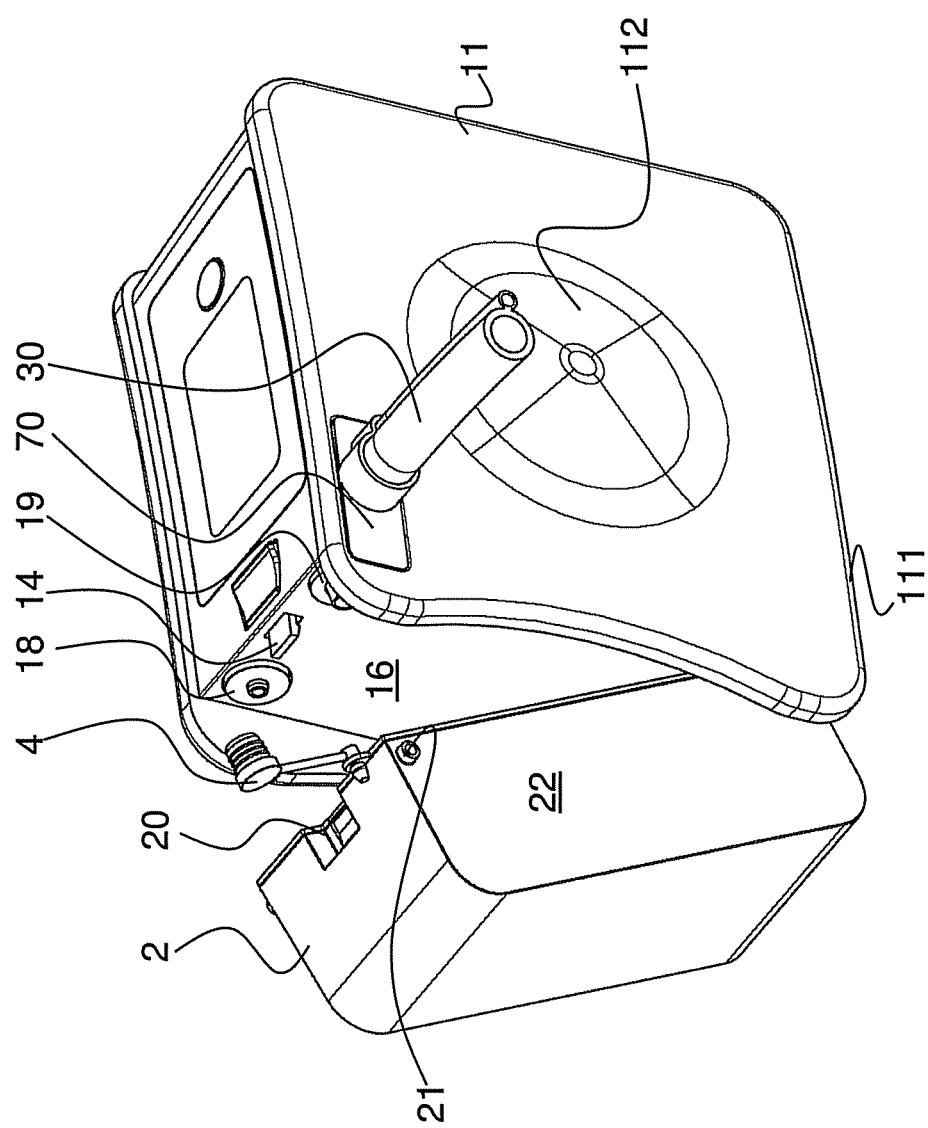
FIG. 3, the aspiration pump unit of FIG. 1 with the fluid collection reservoir partly swiveled out, in perspective view, looking from one side.

The pump assembly housing 1 is essentially shaped as a cuboid, having a rear wall 10, a front wall 11 running approximately parallel to the latter, a first side wall 16 arranged between these walls, a second side wall 17 running approximately parallel to the first side wall 16, and a top wall 12 and a bottom wall not visible in the figure. The housing 1 is preferably made of plastic or metal. The rear wall 10 and the front wall 11 can be configured planar. However, as can be seen in FIG. 3, the front wall 11 can also have a central, outwardly projecting bulge 112. The rear wall 10 can be curved inward, so as to conform to the shape of the human body and thus lie better against the body. The front wall 11 can also be curved accordingly.

Preferably, the rear wall 10 and the front wall 11 have the largest wall surfaces. Furthermore, the top and bottom wall 12 are configured longer than the side walls 16, 17, so that the housing 1 forms a horizontally placed cuboid.

In the figures, the means of fastening for corresponding clamps and straps for carrying the portable aspiration pump unit are not depicted. However, they are preferably located on the rear wall or the side walls of the housing.

Operating elements for the pump assembly 6 are present in the housing 1. These elements are preferably arranged in the top wall 12. In the example depicted here, a main switch 5 is present to turn the unit or the device on and off. Furthermore, there is a display and operating field 15, where status information about the device, the suction process, and other information helpful to an optimal aspiration can be displayed or consulted. For example, the air flow through the secretion line 30 can be metered and presented in the display field 15. It is also possible to arrange a data storage element in the housing 1, in order to save measurement data and show it on the display field 15 by entering proper command instructions.

Furthermore, the vacuum pump 62 or the motor 60 can be activated via this field 15 or desired aspiration parameters can be entered or selected. Preferably, the field 15 is a touch-screen field of familiar kind. However, it is also possible to use, in place of such a field, operating buttons and switches and, optionally, a familiar LCD display. Moreover, these elements can also be arranged in a different wall.

The rear wall 10 and the front wall 11 project by their edges at least beyond the first side wall 16, preferably both side walls and also the bottom and top wall. The field 15 is protected against unintentional activation by the projecting walls 10, 11.

The fluid collection reservoir 2 is likewise approximately cuboid in shape. It has two walls 22 running approximately parallel to each other and being approximately plane, forming the front and rear wall. The same holds for the side walls and the top and bottom wall.

This fluid collection reservoir 2 is held in the housing 1 and can be detached and preferably removed entirely from it. For this, the rear wall 10 and the front wall 11 of the housing have regions, here designated as the front wall edge 110 and rear wall edge 100 that project beyond the first side wall 16. These wall edges 100, 110 are preferably formed curved, having an indentation in their own wall surface. The reservoir 2 is held between these wall edges 100, 110, while the curved regions facilitate the grasping and manual holding of the reservoir 2.

Figure 4:
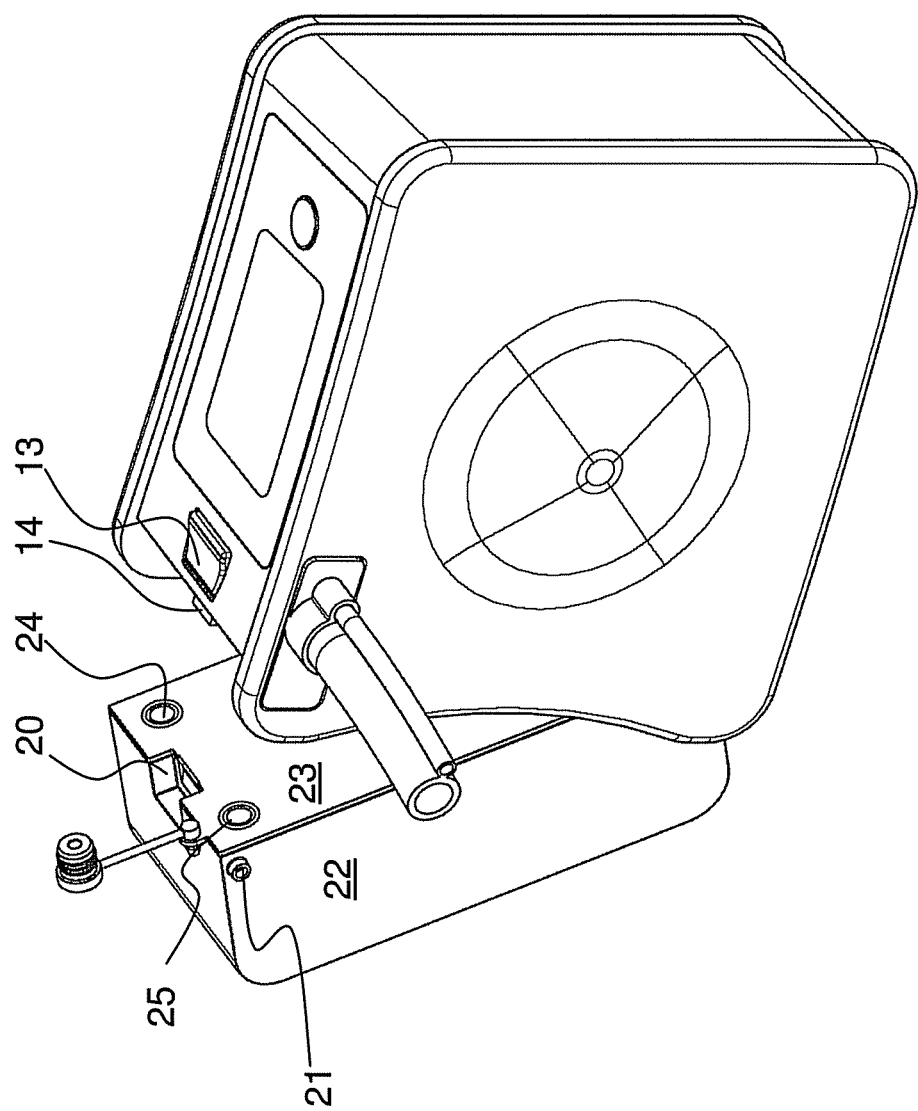
FIG. 4, the aspiration pump unit of FIG. 3 in perspective view looking from a second side.

As can be seen from FIGS. 3 and 4, the reservoir is arranged so that it can be swung in and out between the two edges 100, 110. In its lower region, it is held so that it can swing between the wall edges 100, 110. Preferably, it can be snapped into this position. For this, corresponding bolts are present on the front and rear wall 22 of the reservoir 2 and corresponding recesses are present in the wall edges 100, 110. Of course, the bolts can also be in the wall edges 100, 110 and the recesses in the reservoir 2. Furthermore, other kinds of fastening are also possible, such as allow for a swinging movement and a subsequent removal of the reservoir 2. In at least this region, the shape of the front and rear wall 22 of the reservoir 2 conforms to the shape of the wall edges 100, 110.

The reservoir 2 can be locked to the housing 1 in an upper region. For this, the reservoir 2 has a recess 20, in which a retaining lug 14 of the housing 1 can engage. The retaining lug 14 can be released from engagement with the recess 20 by an unlocking button or switch 13, so that the reservoir 2 can be swung outward. The unlocking button 13 is preferably arranged in the top wall 12. As additional support, the reservoir 2 can be provided with projecting pegs on its front and its rear wall, which are pressed against the wall edges 100, 110, so that the reservoir 2 does not automatically drop out from the device 1 after releasing the locking To connect the housing 1 or assembly 6 to the fluid reservoir 2, a vacuum connector 18 at the housing side and the secretion connector 19 at the housing side are arranged in the housing 1, as can be seen from FIG. 3. The pendants at the reservoir side can be seen in FIG. 4. The vacuum connector at the reservoir side is designated 24 and the secretion connector at the reservoir side is designated 25. Both connectors are arranged in a side wall 23 of the reservoir 2. The vacuum connectors 24, 18 for the connection between vacuum pump 62 and reservoir 2. The secretion connectors 19, 25 connect the reservoir 2 to the adapter 7, which can be connected to the secretion line 30.

If the reservoir 2 is removed, the connector 25 at the reservoir side can be closed off by means of a closure element 4. This is preferably fastened to the reservoir 2, as can be seen in FIG. 4. It has a stem and a closure cap arranged at the end of the stem. The closure cap is suitable for closing off the connector 25. The connector 24 can be closed by a filter (not shown), which automatically closes completely when saturated with moisture. Other types of closure are also possible.

In FIG. 2 it can be seen that the projecting edges of the pump assembly housing 1, namely, a back and a front bottom edge 101, 111, form a standing surface for resting on a surface, such as a table. However, the fluid collection reservoir 2 preferably ends with its bottom floor above this standing surface, so that it hangs free in the housing 1. As can be seen from FIG. 5, however, it is held and guided between the two wall edges 100, 110. Furthermore, one can see that the reservoir 2 projects beyond the housing 1 preferably on only a single side.

Figure 5:
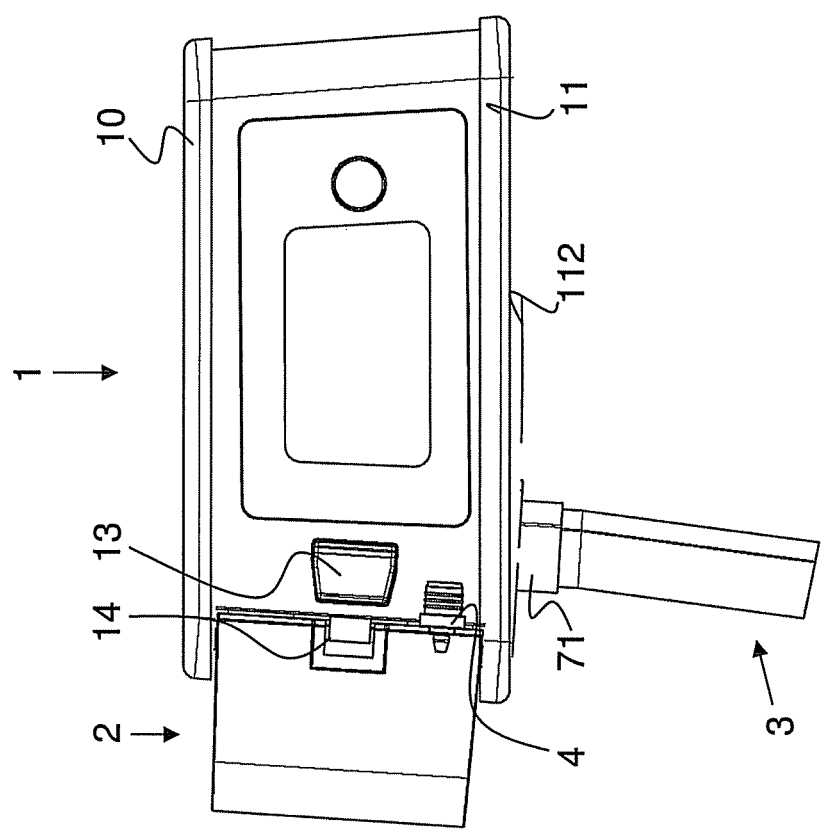
FIG. 5, a top view of the aspiration pump unit of FIG. 1.
Figure 6:
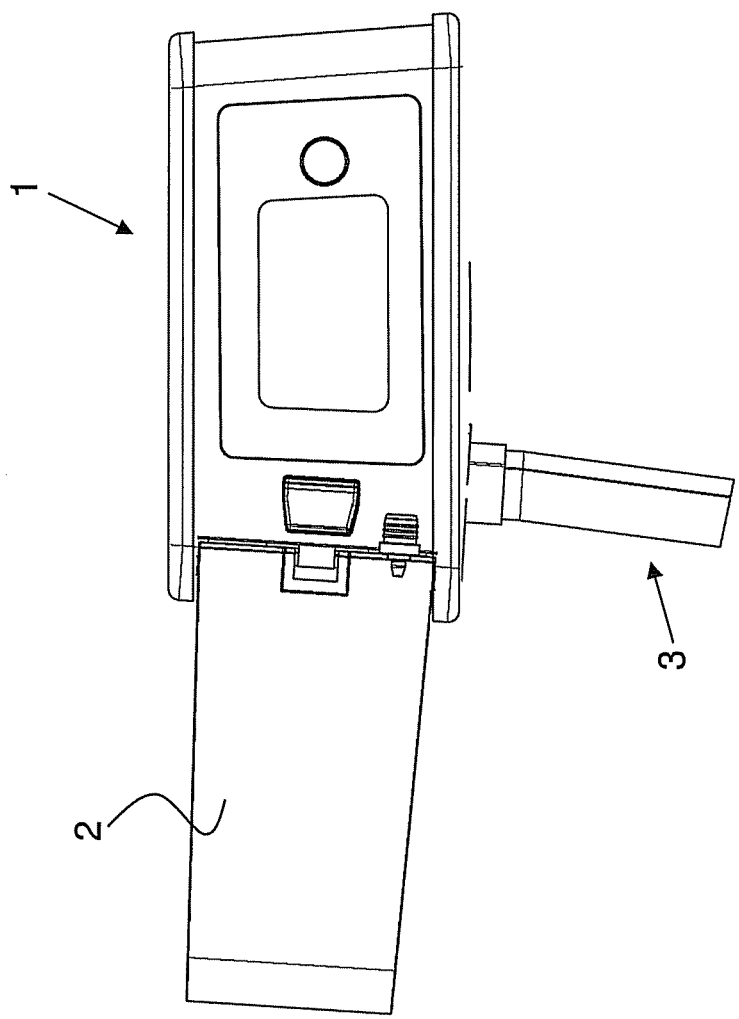
FIG. 6, a top view of the invented aspiration pump unit in a second embodiment.

The size of the reservoir 2 can vary. In FIG. 5, a relatively short reservoir 2 is shown, in FIG. 6 a longer reservoir 2. They need only have the same shape in the region between the wall edges 100, 110, so that they can both be fastened in the same housing 1. The rest of the shape is arbitrary.

Figure 9:
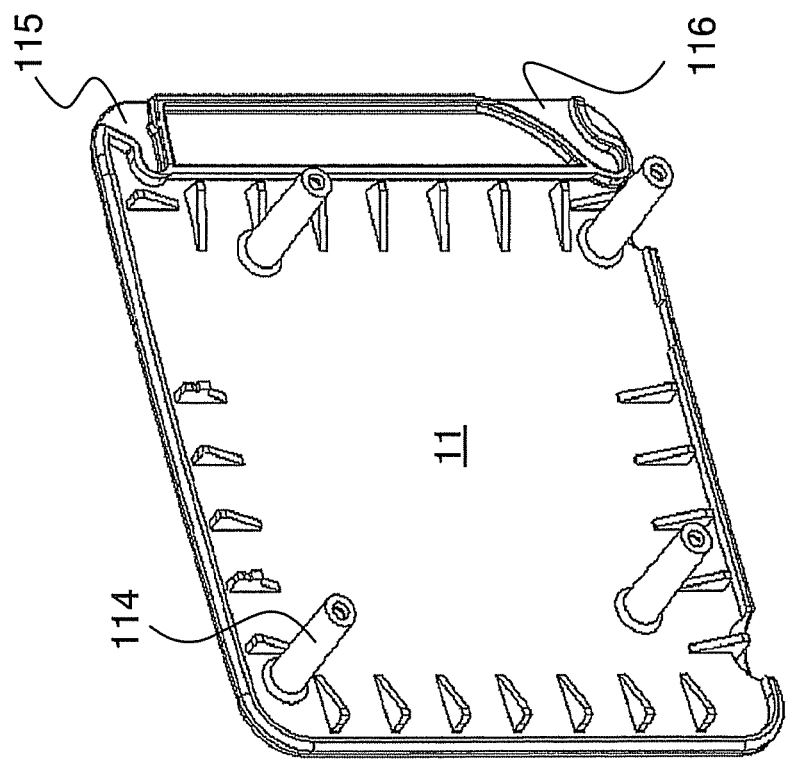
FIGS. 8 and 9, a perspective view of two parts of the housing in a third embodiment.
Figure 8:
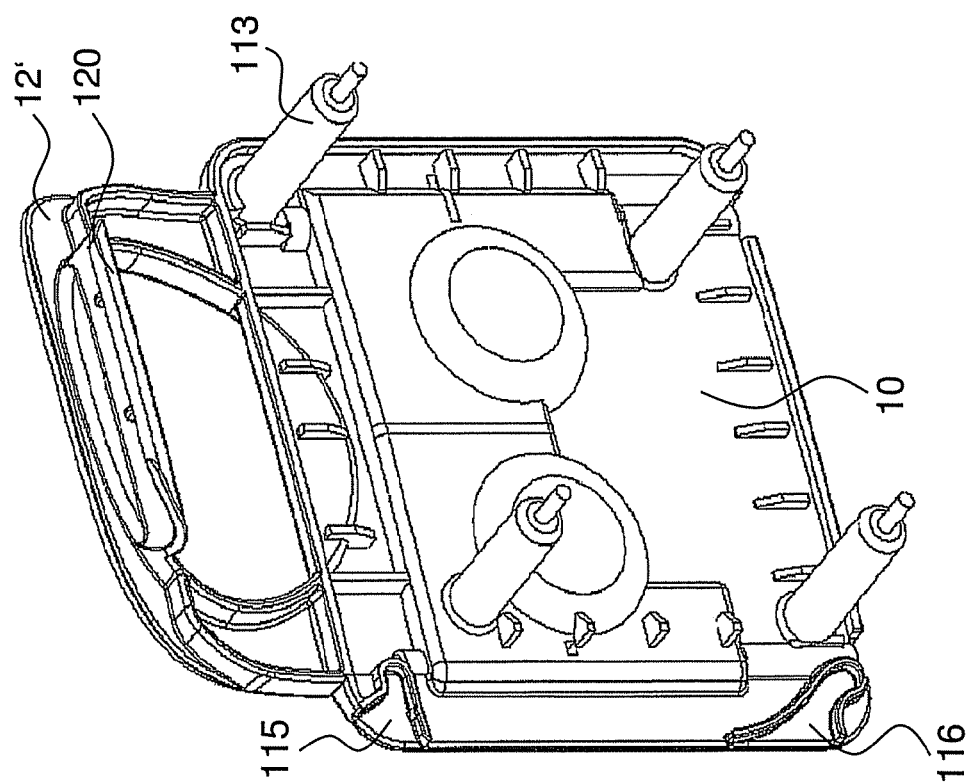

FIGS. 8 and 9 show two opposing parts of a pump assembly housing 1 in a third sample embodiment. These two parts form the rear wall 10 (FIG. 8) and the front wall 11 (FIG. 9) of the housing 1. Both parts are preferably in each case formed in one piece from plastic in an injection molding process.

The two parts 10, 11 are designed such that they can be inserted into one another, with said parts 10, 11 being held spaced apart from one another. For this purpose, perpendicularly projecting insertion mandrels 113, and opposing receiving sleeves 114 which are matched thereto, are arranged at the insides of said parts 10, 11. Said insertion mandrels 113 and receiving sleeves 114 are also preferably injection-molded in one piece with the walls.

One or both of the two walls, here the rear wall 10, can be provided with a handle 12'. A trough 120 is preferably arranged on the handle 12', the bulge of which trough 120 is open in the upward direction. Said trough 120 serves to receive or fasten the patient's tube 30, so that the latter is held so as to be guided along the pump.

At least one part 10, 11, preferably both parts, are provided at their end-side edge with an upper and a lower slotted guide 115, 116. The two opposite upper slotted guides 115 have a widened insertion opening and an adjoining, horizontally-running end region which is aligned inwards away from the edge. The two opposite lower slotted guides 116 likewise have a widened entry region. This however merges, likewise inwards away from the edge, into a lower end region which is aligned obliquely downward. Said slotted guides 115 and 116 serve to hold and retain the fluid collection reservoir 2.

Figure 10:
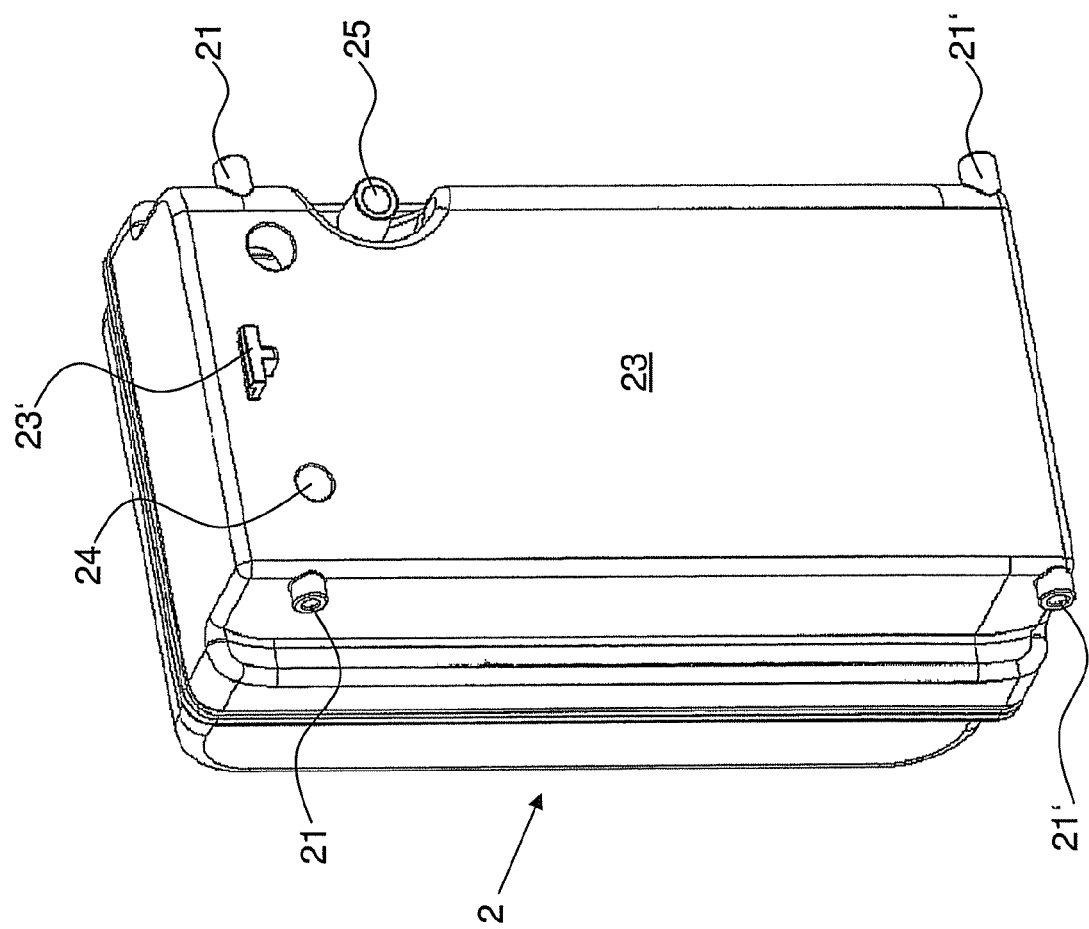
FIG. 10, a perspective view of a fluid collection reservoir suitable for the housing of FIGS. 8 and 9.

A corresponding plastic fluid collection reservoir 2 is shown in FIG. 10. In the region of a side wall 23, said fluid collection reservoir 2 has upper and lower pins or pegs 21, 21' which are integrally injection-molded in one piece onto the rear wall or front wall and project substantially perpendicularly therefrom.

In order to now detachably fasten the collection reservoir 2 to the housing 1, said collection reservoir 2 is first inserted with its lower pins 21' into the lower slotted guide 116 up to the stop, and subsequently snapped with the upper pins 21 into the upper slotted guide 115, or into its end position, by means of a pivoting movement about the pivot axis defined by the end position of the lower slotted guide 116. The same type of fastening is also preferable for the sample embodiments mentioned further above. The pegs can also be arranged on the housing, and the slotted guides on the reservoir. However, other types of fastening are possible.

As can be seen in FIG. 10, in the case of this collection reservoir 2, the vacuum connection 24 at the reservoir and the secretion connection 25 at the reservoir are no longer of the same design as in the sample embodiment above. The adapter piece 70 also need not strictly be arranged in a front or rear wall 10, 11 but can also be arranged at another point of the housing 1, for example in an end side. Furthermore, instead of a recess, the reservoir 2 is provided with an engagement rib 23' for fixing the reservoir 2 to the housing 1, into which engagement rib 23' the retaining lug of the housing 1 can engage. The lug and the recess or rib can also alternatively be arranged on the reservoir or on the housing. These features can be combined with one another in any desired manner, and can also be used in the examples mentioned above.

Figure 12:
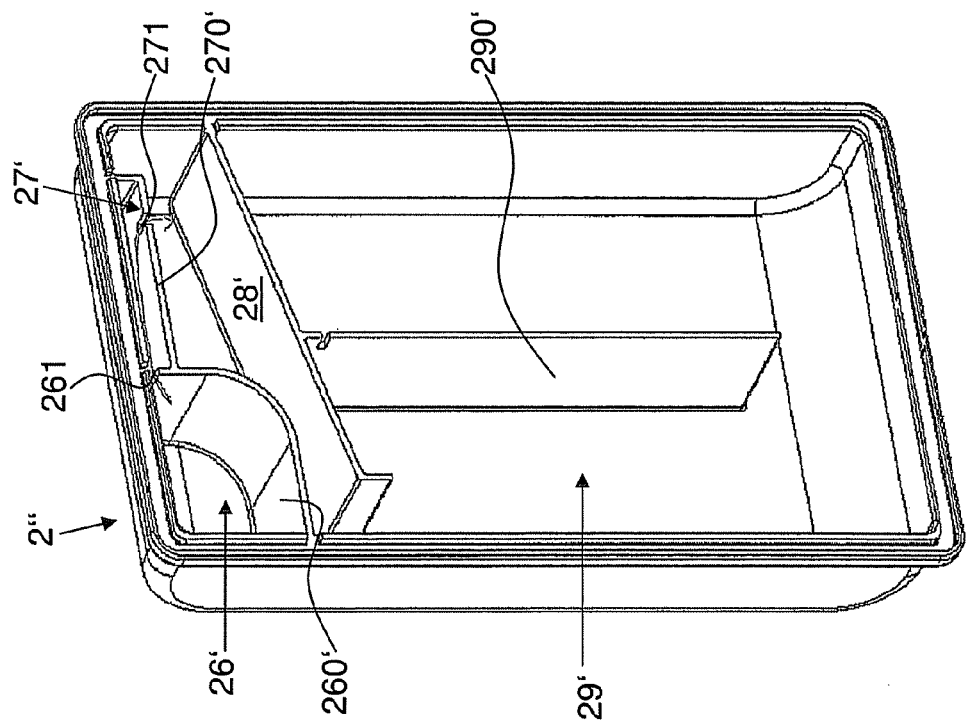
FIG. 12, a perspective view of a second part of the fluid collection reservoir of FIG. 10.
Figure 11:
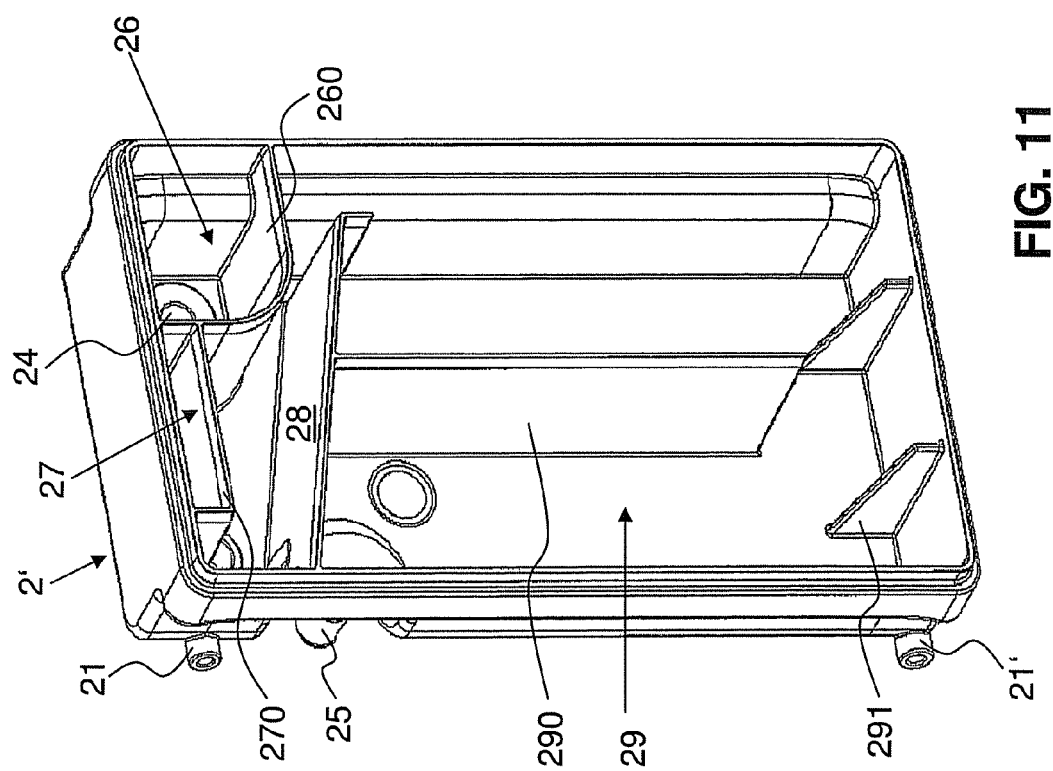
FIG. 11, a perspective view of a first part of the fluid collection reservoir of FIG. 10.

The reservoir 2 can be provided with a single chamber. The interior space of said reservoir 2 is however preferably designed so as to be divided, as shown in FIGS. 11 and 12. This reservoir can be used in all of the sample embodiments. Said reservoir is additionally also suitable for other types of drainage pumps.

The reservoir 2 is composed of two plastic injection-molded parts 2', 2" which are joined to form a common reservoir. Said parts 2', 2" are preferably designed so as to be transparent. The two parts 2', 2" can be plugged together and if appropriate fused to one another. Both parts 2', 2" are provided in the interior space with various ribs, which are described in detail in the following. The two parts 2', 2" have congruent ribs, so that, when said parts 2', 2" are joined together, they form common chambers and regions. The ribs are preferably fused or adhesively bonded to one another when they are joined together, so as to generate an air-tight and liquid-tight connection.

The vacuum connection 24 at the reservoir is arranged in the upper region of the reservoir 2, preferably in the side wall 23 which is provided laterally with the pegs 21, 21' for snapping into the housing 1. The vacuum connection 24 is formed by a continuous opening in said side wall 23. The opening 24 leads into a vacuum chamber 26, 26' which is completely sealingly divided from the rest of the interior space of the reservoir 2 with the exception of a vacuum passage 261. The latter is provided by means of a first curved rib 260 in the first part 2' and a second rib 260', which is of the same shape as said first rib 260, in the second part 2". The passage 261 can be arranged in the first part 2' or, as illustrated here, in the second part 2", or can be arranged at the connecting point of the two ribs 260, 260'. The vacuum passage 261 is preferably arranged in the upper region, adjacent to the upper wall of the reservoir 2.

Following adjacent to this vacuum chamber 26, 26', likewise along the upper wall, is an intermediate chamber 27, 27'. The vacuum passage 261 connects the vacuum chamber 26, 26' to the intermediate chamber 27, 27'. The intermediate chamber 27, 27' is preferably formed by a third rib 270, which is bent at right angles, in the first part 2', and by a congruent rib 270' in the second part 2". Again provided in one of the two parts or in the intermediate region is a passage, referred to here as an intermediate passage 271, which connects the intermediate chamber 27, 27' to the rest of the interior space of the reservoir 2. The intermediate passage 271 is preferably situated in a region remote from the vacuum chamber 26, 26'.

The two passages 261 and 271 are of relatively narrow design. It is however also possible for a plurality of passages to be provided. Said passages should be small enough to prevent as far as possible a return flow of the secretion or of the aspirated fluid, and large enough that the reservoir can be acted on as quickly as possible with the applied vacuum.

Arranged below the intermediate chamber 27, 27' and below the intermediate passage 271 in both parts 2', 2" is in each case one inclined rib 28, 28' which extends downwards from the intermediate passage 271 towards the vacuum chamber 26, 26'. The inclined ribs 28, 28' divide the interior space into an upper and lower region, with the upper region enclosing a significantly smaller volume than the lower region. The inclined ribs (28, 28') preferably extend together over a significant part of the width, but not over the entire width, of the reservoir 2, and over the entire depth of said reservoir 2. In this way, the aspirated fluid must flow downwards along the inclined rib 28, 28'.

The lower region can also be provided with vertically-running dividing ribs 290, 290', 291 which can extend over almost the entire height of the lower region or only over a short lower part thereof.

The secretion connection 25 is arranged in the lower region. The lower region therefore serves to receive the aspirated fluid and forms a secretion chamber 29, 29'. The dividing ribs 290, 290', 291 divide said chamber into sub-chambers which are fluidically connected to one another. Here, however, said sub-chambers prevent the accumulated fluid from surging back and forth. The inclined ribs 28, 28' prevent the fluid spraying into the upper region and, in the event of the reservoir being in a slightly inclined position, prevent the fluid from flowing back into said region. The narrow passage openings and in particular the labyrinth-like arrangement as a result of the intermediate or expansion chamber prevent fluid, which has nevertheless passed into the upper region, from advancing as far as the vacuum connection.

In one embodiment which is not shown, the ribs are arranged in only one part, and the second part is of flat design and serves as a cover.

The intermediate chamber 27, 27' is optional but preferable, since it avoids a direct connection between the vacuum chamber 26, 26' and the secretion chamber 29, 29'.

All of the fluid collection reservoirs described above can be produced in different sizes.

The invented aspiration pump unit enables a simple and secure replacing of the fluid collection reservoir and affords the patient a heightened mobility.

Figure 13:
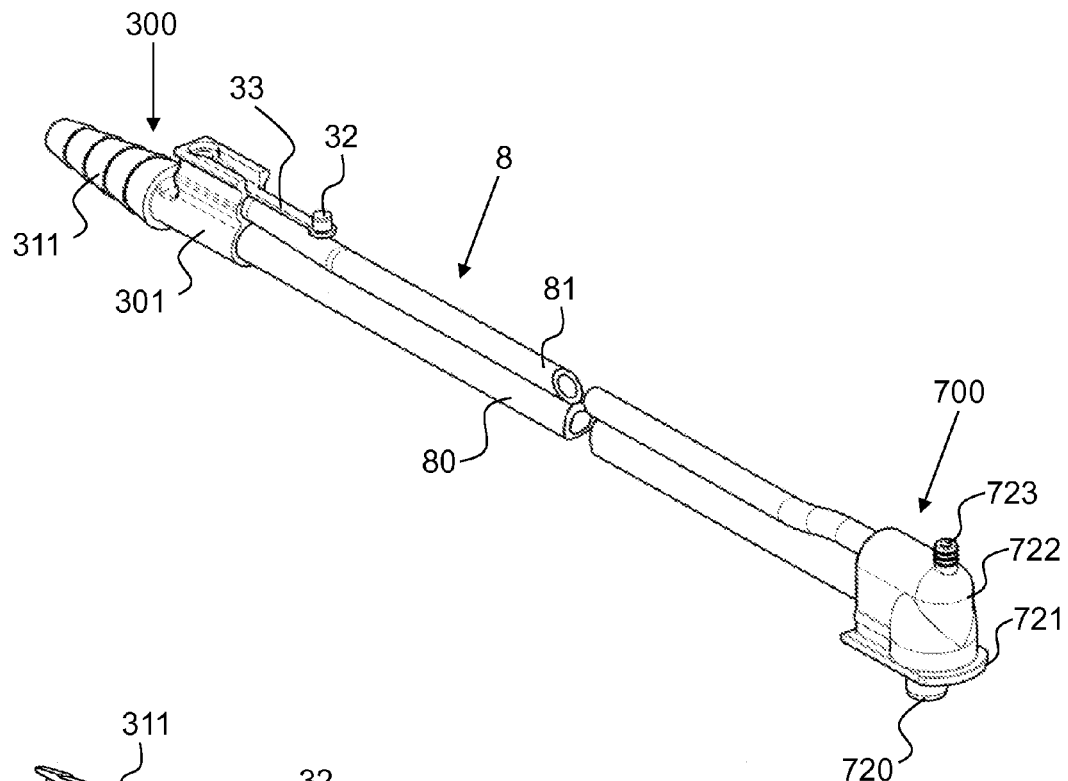
FIG. 13, a perspective view of a drainage tube unit according to a fourth embodiment of the invention.

FIG. 13 shows another embodiment of a suction or drainage tube unit as used in the drainage aspiration devices mentioned at the outset. It is composed mainly of a tube system 8 with two or more tubes 80, 81, a pump-side attachment part 700 and preferably, but not necessarily, a patient-side attachment part 300. According to the invention, however, an individual single-lumen drainage tube can also be used.

The lines or tubes 80, 81 shown here are preferably single-lumen tubes independent of each other. They are preferably made of silicone or PVC. They extend separate from each other at their ends. Between the ends, they can be adhesively bonded to each other, welded to each other or otherwise connected. In the figures, the tubes are not shown at their full length and are instead interrupted.

The two tubes preferably have different diameters. The thicker tube 80 forms an underpressure and drainage line for aspirating the body fluid. The thinner tube 11 forms a service line which, for example, permits the above-described or similar pressure measurement and/or cleaning of the drainage line. Both applications can be carried out jointly but one after the other if the suction unit at the pump-side end of the service line has a valve which is closed for the underpressure measurement during the aspiration procedure. During the cleaning mode, however, the valve is opened. The service line can also be used in other known ways.

The lines or two tubes 80, 81 preferably extend parallel to each other along approximately the entire length, and their ends in particular open out in parallel, but spaced apart from each other, into the respective attachment parts or elements 700, 300. Spaced apart means that they can bear on each other or that they can leave a space free between them. At least in one of the two parts, they protrude inwards on the same face of the attachment part. The ends are inserted into the attachment parts 700, 300, adhesively bonded in them or otherwise secured.

The pump-side attachment 700 will first be described below. Pump-side in this context, however, simply means remote from the patient. Instead of being in a pump housing, the attachment part can instead also be arranged in a fluid collection container or other unit remote from the patient. Therefore, where the term pump-side is used below, this also means the container side.

The pump-side attachment part 700 is preferably made of plastic by injection moulding, and it is preferably designed in one piece.

Figure 16:
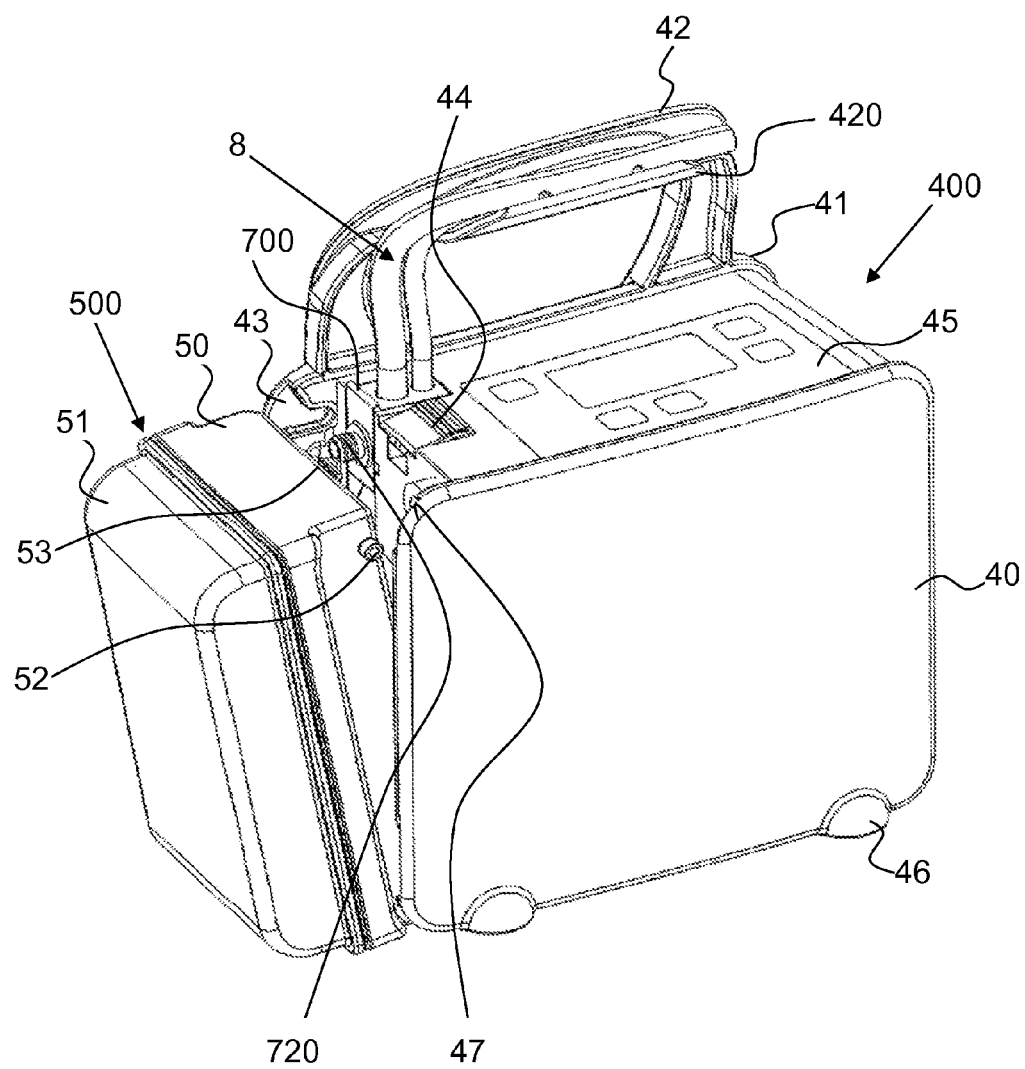
FIG. 16, a perspective view of a drainage pump device with a variation of a pump-side attachment part of the drainage tube unit according to the invention.

It has a substantially cuboid main body 700, which is here provided with a peripheral flange 721. With this flange 721, the part 700 can be introduced with a form fit into a corresponding recess of the pump housing and held therein, as is shown in FIG. 16.

Figure 14:
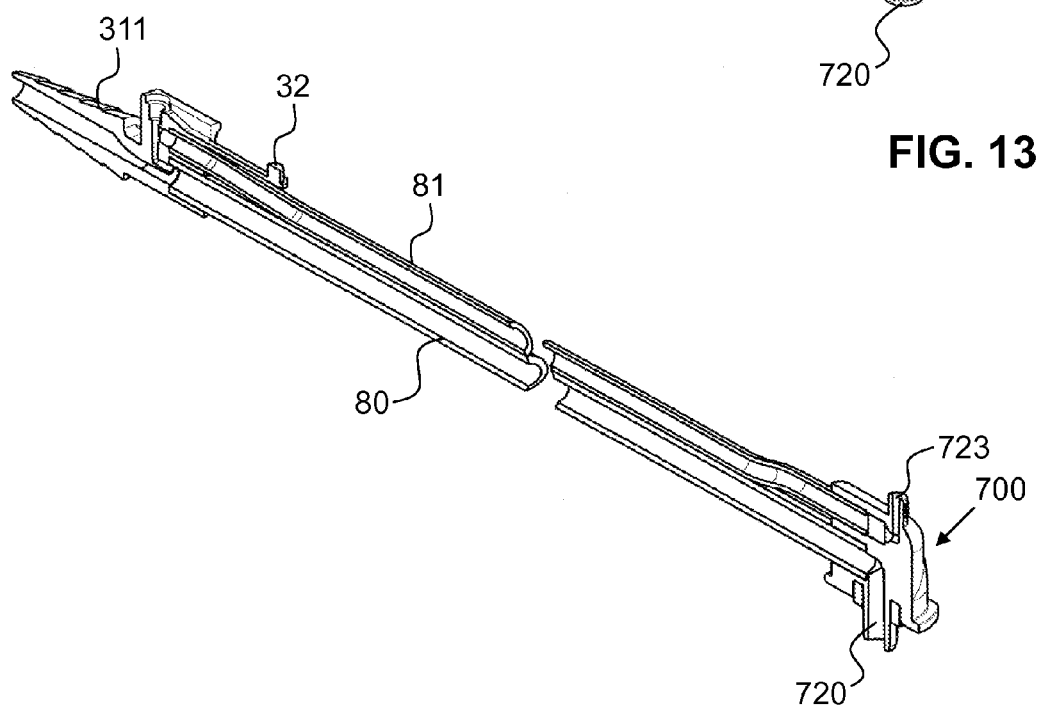
Figure 15:
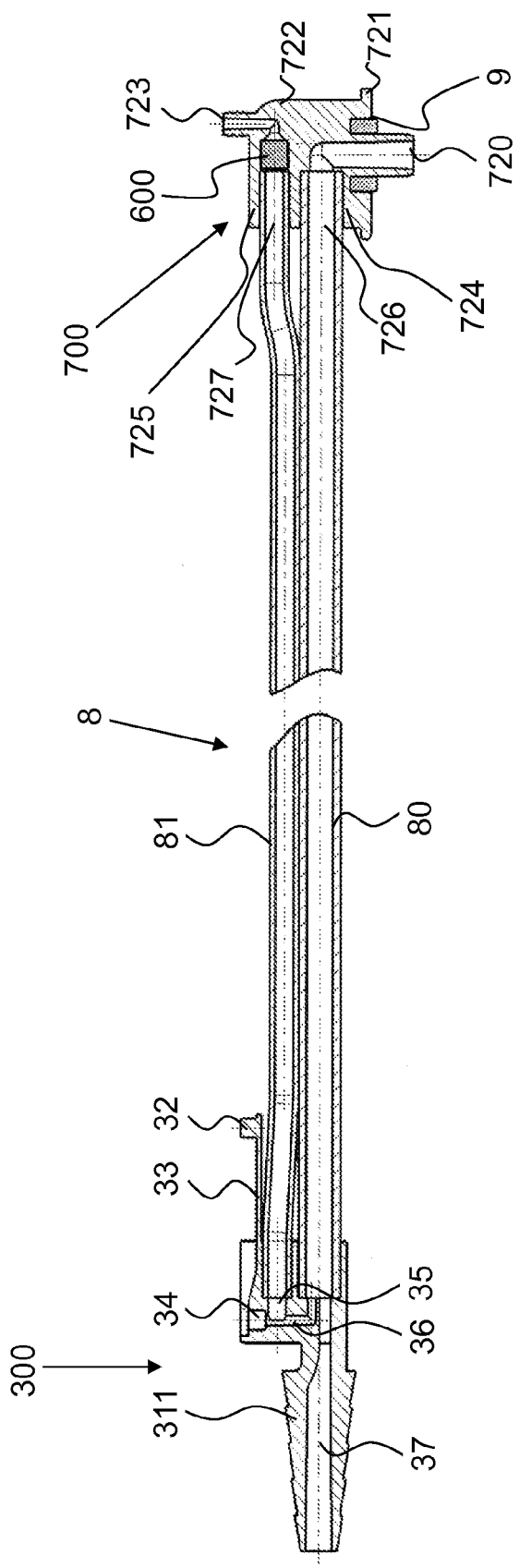
FIG. 15, a longitudinal section through the drainage tube unit according to FIG. 13.

As can be seen from FIGS. 14 and 15, the attachment part 700 has two channels 724, 725, and the pump-side ends of the drainage and service tubes 80, 81 are inserted into the mouth openings, or patient-side connection elements 726, 727, that lie parallel to each other but spaced apart from each other.

A filter 600 is preferably arranged in the pump-side service channel 725. This, for example, is a hydrophobic filter and/or a bacterial filter. The service channel 725 then narrows and bends off at right angles with respect to the mouth. It ends in a service inlet 723 that protrudes in the form of a connector piece from the main body 722. This service inlet 723 serves for connection to a service unit of the suction device.

The pump-side drainage channel 724 also bends off at right angles with respect to its mouth and likewise ends in a connector piece, the pump-side drainage outlet 720, protruding from the main body 722. This outlet 720 serves for connection to a fluid collection container. The outlet 720 is here arranged at right angles to the mouth of the tube 80, but it can also be arranged on a different face of the main body 722 than the mouth face. The same applies for the service inlet 723 in relation to the mouth of the service tube 80.

The aspirated fluid passes through the drainage outlet 720 into the container. To ensure leaktightness, a peripheral groove can be provided round the drainage outlet 720 in the main body 722. The groove can be provided with a sealing ring. The drainage outlet 720 is preferably arranged on a face of the main body 722 that lies opposite the face with the service inlet 723.

Instead of the pump-side attachment part 700 or end connector described here, a more simply configured part can also be used that is held on or in the pump housing 400. For example, the service channel and the service attachments can be dispensed with if only an individual drainage tube and no service tubes are to be attached.

On the patient side, it is possible, but not necessary, for a patient-side attachment part 300 to be present. If it is present, it is preferably also made of plastic by injection moulding. It too is preferably designed in one piece. A variant with a service tube is described below. It goes without saying that the part has a simpler design, particularly without connection channel and service channel, if no service channel is to be connected, but instead only an individual drainage tube.

The patient-side attachment part 300 has a main body 301 with two mouths for the patient-side ends of the drainage tube 80 and of the service tube 81, which mouths are parallel to each other but spaced apart from each other. A patient-side drainage inlet 311, formed integrally on this main body 301, has a conical shape and is provided with steps and narrows towards its free end. It has a Christmas tree shape in cross section. The drainage inlet 311 preferably extends approximately in axial alignment with the mouth of the patient-side end of the drainage tube 80, such that the patient-side drainage channel 37 in the interior of the attachment part extends approximately in a straight line.

The patient-side end of the service tube 81 opens into a mouth of a patient-side service channel 35, which preferably has a smaller diameter than the drainage channel 37. The channel 37, also like all the other channels described, has a step that serves as an abutment for the tube 81. The mouths described above are understood as extending as far as these steps.

The service channel 723 ends in the main body 301 and there opens into a connection channel 36, which is preferably perpendicular to the service channel 723. The connection channel 36 has the same diameter as or preferably a smaller diameter than the service channel 35. It terminates at one end in a right-angled bend in the drainage channel 37, preferably at the step to the mouth. Its other end forms an opening 34 to the outside, which opening 34 is preferably arranged perpendicular to the mouths in the main body 301.

This opening 34 is closed by a sealing closure 32, in this case a stopper. In the figure, it is shown still in the open state, it is preferably already closed in this configuration, In fact it is preferably already closed on ejection from the injection moulding machine, that is to say long before the tubes 80, 81 are secured.

The sealing closure 32 is preferably produced in one piece with the rest of the attachment part 300 and, as is shown, is therefore connected to the main body 301 via a band 33. This opening permits the one-piece production of this attachment part.

FIG. 16 shows a drainage pump device with which the drainage tube unit is preferably used. It serves to aspirate body liquids or fluids in the medical field, for example during or after surgical interventions, but also for wound drainage, thorax drainage, or for liposuction.

However, the tube unit can also be used in other drainage pump devices. It is preferable, but not essential, that the fluid collection container and, in the case of service tubes, also the pump unit can be connected to each other by means of the pump-side attachment part 700 without further intermediate lines.

The drainage pump device shown here has a pump housing 400 which accommodates a vacuum pump or suction pump and electronics for operating the pump and for evaluating measured values obtained by way of the service tube.

The pump housing 400 preferably has a cuboid shape with a front wall 40, a rear wall 41, a handle 42 and feet 46. On an upper face of the housing 400, there is an operating panel 45 for operating the pump, preferably with a display.

The front wall 40 and the rear wall 41 jut out at one side and form a recess for a fluid collection container 500. This fluid collection container 500 is preferably composed of two container halves 50, 51 and is made of a transparent plastic.

The container 500 can be secured releasably on the pump housing 400, preferably being swivelled in and engaged in this position. For this purpose, the front wall 40 and the rear wall 41 of the pump housing 400 have upper and lower slide guides in which upper and lower securing pins 52 of the container 500 engage. Only one upper pin can be seen in the figure. The lower pins are already engaged, as can be seen from the oblique position of the container 500.

The container 500 has a hook 53 which is directed towards the housing 400 and in which a flip switch 44 of the housing 400 engages with a corresponding projection. In this way, the container 500 is fixed releasably on the housing 400.

Figure 18:
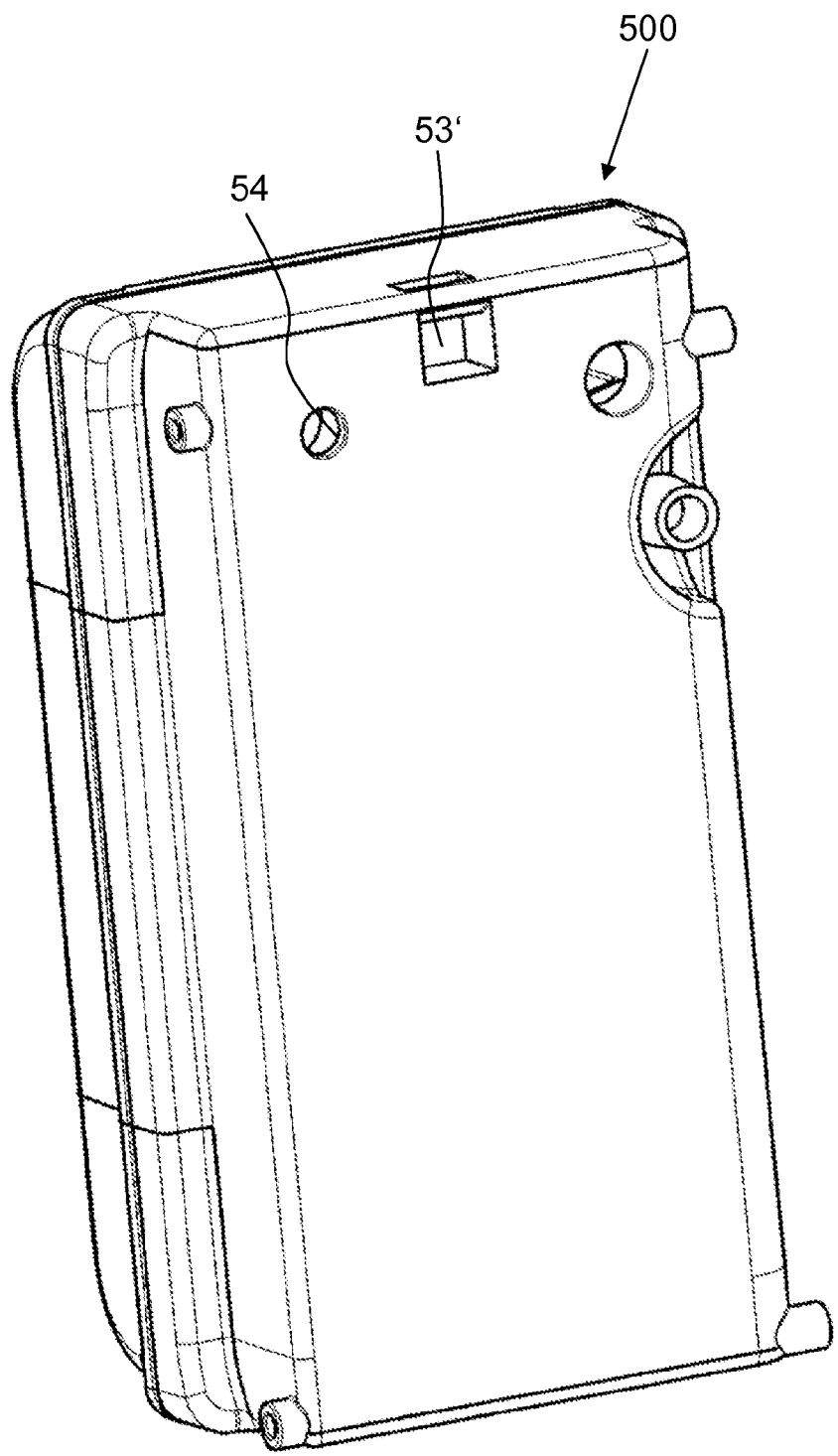

In the variant according to FIG. 5 the flip switch 44 comprises a hook 44' which engages with a recess 53' of the fluid collection container 500 shown in FIG. 18.

Facing the container 500, a suction connector 47 is provided on the housing 400. It has the shape of a nozzle, which engages in a corresponding opening of the container 500. In this way, an underpressure can be generated in the container 500 by means of the suction pump.

The housing 400 also has a substantially cuboid recess 49 into which the pump-side attachment part 700 of the drainage tube unit can be inserted and is held releasably therein with a form fit. In the variant according to FIG. 4, the recess 48 comprises plane side walls, so that the pump-side attachment part should comprise, contrary to the attachment part shown in FIGS. 1 to 3, plane side walls as well.

Figure 17:
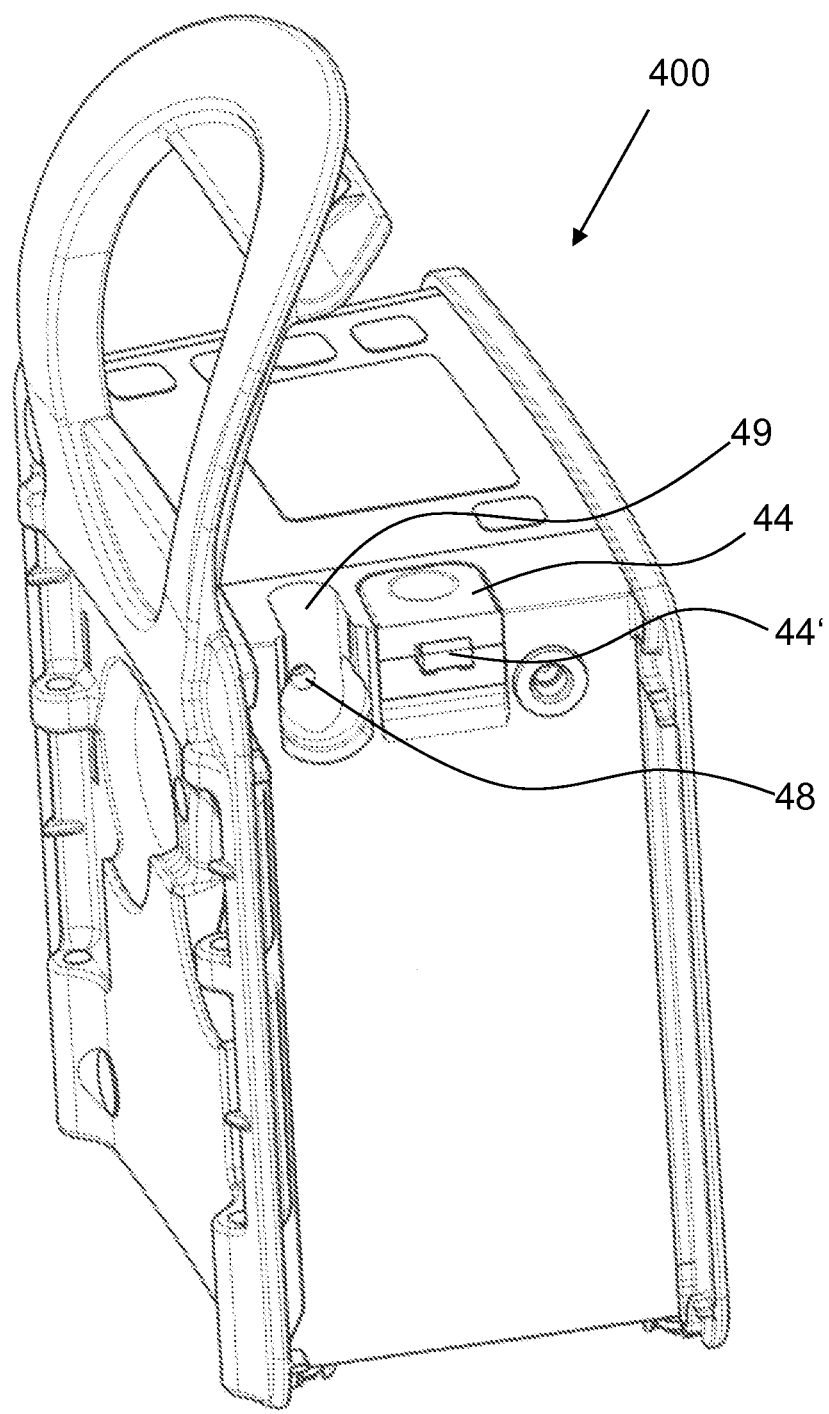
FIG. 17, a perspective view of a variation of the pump housing with its seat for the pump-side attachment part, and FIG. 18, a perspective view of the fluid collection container with its attachment opening for pluggable connection to the attachment part.

In the variant according to FIG. 17 the recess 49 comprises two plane and parallel to each other extending side walls and a curved, concave side wall connecting these two. This recess 49 matches the embodiment according to FIGS. 13 to 15.

The container-side drainage outlet 720 of the attachment part 700 of both variants is oriented towards the container 500. Through it the aspirated fluid passes into the container 500. As can be seen clearly in FIG. 18, the fluid collection container 500 has a corresponding attachment opening 54. Alternatively, the attachment part 700 can also be provided with an opening and the fluid collection container can be provided with a connector piece that matches said opening. In any case, a sealed connection is established, with a sealing means preferably being provided on at least one side, i.e. on the side of the attachment part or on the side of the fluid collection container. The sealing means is preferably a sealing ring made of an elastomer material. Here, it is an elastomer sealing ring 9 as shown in FIG. 15. However, other known ways of making a plug-type connection air-tight and liquid-tight are possible.

At right angles thereto, the tube system 8 with the two tubes 80, 81 opens into the pump-side attachment part 700. The tube system 1 in this example is routed along the housing 400 in a channel 420 arranged on the handle 42.

It will be seen from FIG. 17 that the pump housing 400 has a service opening 48 for receiving the service inlet 23 of the pump-side attachment part 700. The service inlet 723 of the attachment part 700 protrudes into the pump housing 400 and is connected to a corresponding control and/or evaluation unit. Depending on the particular application, an air-tight or liquid-tight connection is also present here. Here too, connector piece and opening can be provided the other way round.

Variants of the abovementioned example are conceivable. For example, the pump-side attachment part can be inserted in the housing or held on the latter at another place. The attachments can, for example, be at another angle to one another. The pump-side attachment part can be designed, for example, with a conical, cylindrical or other suitable shape.

The drainage pump unit according to the invention allows the fluid collection container to be replaced or emptied without removing the drainage tube and, therefore, without disturbing the patient.

The invention claimed is:

1. A drainage pump unit for aspirating body fluids by means of a suction pump, said drainage pump unit comprising a drainage pump device with a pump housing for receiving said suction pump, and a fluid collection container that can be secured releasably on said pump housing, wherein said suction pump creates an underpressure in said fluid collection container, wherein said drainage pump housing also comprises a recess for accommodating a pump-side attachment part, said pump-side attachment part having a connection element for connection to a patient-side drainage tube, wherein said pump-side attachment part is held releasably on said pump housing, and said pump-side attachment part connects said patient-side drainage tube with said fluid collection container, and wherein said fluid collection container can be removed from said pump housing without having to remove said pump-side attachment part from said pump housing.

2. The drainage pump unit according to claim 1, wherein said attachment part has a connector piece onto which an attachment opening of said fluid collection container can be fitted, said connection element and said connector piece being connected to each other via a drainage channel extending through said attachment part.

3. The drainage pump unit according to claim 1, wherein said attachment part has an attachment opening into which a connector piece of said fluid collection container can be inserted, said connection element and said attachment opening being connected to each other via a drainage channel extending through said attachment part.

4. The drainage pump unit according to claim 1, wherein said attachment part can be releasably fitted into said recess.

5. The drainage pump unit according to claim 1, wherein said recess is located in a wall of said pump housing directed towards said fluid collection container.

6. The drainage pump unit according to claim 5, wherein said recess extends as far as an edge of said wall and thus forms a corner piece.

7. The drainage pump unit according to claim 6, wherein said edge is an upper edge of said pump housing.

8. The drainage pump unit according to claim 1, wherein said attachment part is held in a form-fit engagement in said recess of said pump housing.

9. The drainage pump unit according to claim 1, wherein said recess in said pump housing has a substantially cuboid shape, and said attachment part has a substantially cuboid main body.

10. The drainage pump unit according to claim 2, wherein said connection element and said connector piece are arranged on two different sides of said attachment part.

11. The drainage pump unit according to claim 10, wherein said connection element and said connector piece are arranged on two sides lying at right angles to each other.

12. The drainage pump unit according to claim 11, wherein said connection element and said attachment opening are arranged on two different sides of said attachment part.

13. The drainage pump unit according to claim 12, wherein said connection element and said attachment opening are arranged on two sides lying at right angles to each other.

14. The drainage pump unit according to claim 1, wherein said attachment part is designed in one piece.

15. The drainage pump unit according to claim 1, wherein said attachment part has a patient-side connection element for connection to a service tube, a pump-side connection element for connection to a service unit arranged in said pump housing, and a service channel that connects said two connection means and extends through said attachment part.

16. The drainage pump unit according to claim 15, wherein said patient-side connection element for connection to said service tube and said connection element for connection to said patient-side drainage tube are arranged on said same side of said attachment part.

17. The aspiration pump unit as claimed in claim 1, wherein said pump-side attachment part is configured to accommodate a double-lumen patient's tube consisting of secretion tube and metering tube.

* * * * *